(12) United States Patent
Kojima

(10) Patent No.: US 9,131,952 B2
(45) Date of Patent: Sep. 15, 2015

(54) FLUID EJECTION DEVICE, FLUID EJECTION METHOD, AND MEDICAL APPARATUS

(75) Inventor: Hideki Kojima, Matsumoto (JP)

(73) Assignee: Seiko Epson Corporation, Tokyo (JP)

(*) Notice: Subject to any disclaimer, the term of this patent is extended or adjusted under 35 U.S.C. 154(b) by 920 days.

(21) Appl. No.: 13/347,252

(22) Filed: Jan. 10, 2012

(65) Prior Publication Data

US 2012/0176431 A1 Jul. 12, 2012

(30) Foreign Application Priority Data

Jan. 12, 2011 (JP) ................................. 2011-003724

(51) Int. Cl.
*A61B 17/32* (2006.01)
*A61B 17/3203* (2006.01)
*A61B 19/00* (2006.01)
*A61B 17/00* (2006.01)

(52) U.S. Cl.
CPC .............. *A61B 17/3203* (2013.01); *A61B 19/46* (2013.01); *A61B 2017/00075* (2013.01); *A61B 2017/00154* (2013.01); *A61B 2019/464* (2013.01)

(58) Field of Classification Search
CPC ..................... A61B 17/3203; A61B 17/32037; A61B 2017/00154; A61B 2017/00194; A61B 2017/00172
See application file for complete search history.

(56) References Cited

U.S. PATENT DOCUMENTS

| | | | | |
|---|---|---|---|---|
| 5,643,302 | A * | 7/1997 | Beiser et al. | 606/167 |
| 5,788,667 | A * | 8/1998 | Stoller | 604/22 |
| 6,451,017 | B1 * | 9/2002 | Moutafis et al. | 606/41 |
| 6,629,948 | B2 * | 10/2003 | Rockley et al. | 604/22 |
| 2002/0095147 | A1 * | 7/2002 | Shadduck | 606/41 |
| 2003/0167053 | A1 * | 9/2003 | Taufig | 604/542 |
| 2006/0100606 | A1 * | 5/2006 | Dobak, III | 604/542 |
| 2006/0156875 | A1 | 7/2006 | McRury et al. | |
| 2006/0271033 | A1 * | 11/2006 | Ein-Gal | 606/41 |
| 2008/0114341 | A1 * | 5/2008 | Thyzel | 606/11 |
| 2009/0043480 | A1 * | 2/2009 | Seto et al. | 701/103 |

FOREIGN PATENT DOCUMENTS

| | | |
|---|---|---|
| JP | 2006-010206 | 1/2006 |
| JP | 2006-198409 | 3/2006 |
| JP | 2009-045167 | 3/2009 |
| JP | 2010-051896 | 3/2010 |
| JP | 2010-053767 | 3/2010 |
| JP | 2010-057531 | 3/2010 |

\* cited by examiner

*Primary Examiner* — Jonathan W Miles
(74) *Attorney, Agent, or Firm* — Workman Nydegger

(57) ABSTRACT

A fluid ejection device for ejecting a fluid to incise or excise a target includes: a fluid supplying unit which supplies the fluid; an operation unit to which the fluid supplied from the fluid supplying unit continues; a fluid ejection tube which ejects the fluid continuing to the operation unit; an ejection mode selecting unit which allows a predetermined ejection mode to be selected; an acceleration sensor which detects an operation acceleration of the operation unit; and a controller which controls ejection of the fluid, using a preset acceleration that is set on the basis of the ejection mode that is selected, and the operation acceleration detected by the acceleration sensor.

13 Claims, 7 Drawing Sheets

FLUID EJECTION DEVICE, FLUID EJECTION METHOD, AND MEDICAL APPARATUS

BACKGROUND

1. Technical Field

The present invention relates to a fluid ejection device, a fluid ejection method, and a medical apparatus using this fluid ejection device.

2. Related Art

A fluid ejection and severance control system for ejecting a pressurized fluid to sever a tissue is known in the related art. In this fluid ejection and severance control system, ejection power of a fluid is controlled by an output (pressure) of a pump. Pressure control methods for the pump may include a method in which a sensor for monitoring the flow rate and pressure of the pump or end effector is added, or a method in which an operator uses a foot switch to input an output change command to a console (see, for example, JP-A-2006-198409).

According to JP-A-2006-198409, when excising a target tissue with the end effector held in the hand, the operator can control ejection power but the degree of excision may vary depending on the way the end effector is moved. For example, in the case where a relatively broad range is to be cut superficially, the end effector needs to be moved finely. However, if the movement of the end effector is stopped, the cutting may become deep more than necessary. Meanwhile, in the case where a specific narrow part is to be excised, if the hand accidentally shakes, the ejected fluid may hit and excise other parts than the site to be excised. Thus, there is a problem that excision and incision cannot be carried out as the operator intends.

SUMMARY

An advantage of some aspects of the invention is to solve at least a part of the problems described above, and the invention can be implemented as the following forms or application examples.

APPLICATION EXAMPLE 1

This application example of the invention is directed to a fluid ejection device which ejects a fluid to incise or excise a target. The device includes: a fluid supplying unit which supplies the fluid; an operation unit to which the fluid supplied from the fluid supplying unit continues; a fluid ejection tube which ejects the fluid continuing to the operation unit; an ejection mode selecting unit which allows a predetermined ejection mode to be selected; an acceleration sensor which detects an operation acceleration of the operation unit; and a controller which controls ejection of the fluid, using a preset acceleration that is set on the basis of the selected ejection mode, and the operation acceleration detected by the acceleration sensor.

Here, the selection of the ejection mode refers to, for example, selecting a mode for incising or excising a broad range, or a mode for incising or excising a narrow range.

According to this application example, the movement at the time when the operator operates the operation unit is detected as an operation acceleration by the acceleration sensor, and whether to eject the fluid or not is controlled according to a preset acceleration that is set on the basis of the selected ejection mode, and the operation acceleration. Therefore, the operator can perform appropriate incision or excision as the operator intends, whether in the case where a broad range is to be cut superficially or in the case where a narrow range is to be cut to an appropriate depth.

APPLICATION EXAMPLE 2

In the fluid ejection device according to the above application example, it is preferable that the predetermined ejection mode includes a broad range mode for incising or excising a broad range of the target, and that in the case where the broad range mode is selected, the controller ejects the fluid when the operation acceleration is greater than the preset acceleration, and stops ejecting the fluid when the operation acceleration is equal to or smaller than the preset acceleration.

Thus, in the case where a relatively broad range is to be cut superficially, when the operation acceleration is equal to or greater than the preset acceleration, for example, the fluid is ejected if the operation unit is moved quickly, whereas the ejection of the fluid stops if the movement of the hand is slowed down or stopped. Therefore, ejection is not carried out continuously at the same spot and unnecessarily deep cutting can be prevented.

APPLICATION EXAMPLE 3

In the fluid ejection device according to the above application example, it is preferable that the predetermined ejection mode includes a narrow range mode for incising or excising a narrow range of the target, and that in the case where the narrow range mode is selected, the controller ejects the fluid when the operation acceleration is smaller than the preset acceleration, and stops ejecting the fluid when the operation acceleration is equal to or greater than the preset acceleration.

In the case where a specific site is to be excised, when the operation acceleration is equal to or smaller than the preset acceleration, for example, when the movement of the operation unit is small, excision can be permitted. If the hand accidentally shakes to make a large movement and consequently the operation acceleration is determined as equal to or greater than the preset acceleration, the ejection is stopped. Thus, excision of an unintended site can be prevented.

APPLICATION EXAMPLE 4

It is preferable that the fluid ejection device according to the above application example further includes an information output unit which outputs information about whether to eject the fluid or not, using the ejection mode that is selected, the preset acceleration and the operation acceleration.

Here, the information output unit maybe, for example, a sound-based output or a visually recognizable output unit such as light or screen display.

For example, the fluid can be ejected when an output of a sound or the like is given by the information output unit, and the ejection can be stopped when the movement of the hand is stopped. That is, in the case of operation within a certain range of operation acceleration, the user can be notified of whether the current state is suitable for ejection or not, via sound, light, screen display or the like. The user can control an ejection switch according to the output of the information output unit. Therefore, the operator can perform operation under intended ejection conditions.

APPLICATION EXAMPLE 5

In the fluid ejection device according to the above application example, it is preferable that the operation unit is a pulsation generator which generates a pulse fluid, and that the controller is a controller which controls ejection of the pulse fluid.

As the pulsation generator which generates a pulse fluid is used as the operation unit, a small-sized device that is easy to operate can be realized. Moreover, fluid ejection forms in excising or incising the target includes a continuous flow (also referred to as jet flow) and a pulse flow. The pulse flow has excellent characteristics such as the capability to excise, incise or fragment a living tissue selectively by a small volume of fluid compared with the continuous flow. Thus, when the pulse flow is used, too, the movement at the time when the operator operates the operation unit (pulsation generator) is detected by the acceleration sensor, and whether to eject the pulse fluid or not is controlled according to the preset acceleration that is set on the basis of the selected ejection mode, and the operation acceleration. Therefore, the operator can perform appropriate incision or excision as the operator intends, whether in the in the case where a broad range is to be cut superficially or in the case where a narrow range is to be cut to an appropriate depth.

APPLICATION EXAMPLE 6

This application example of the invention is directed to a medical apparatus including the fluid ejection device according to any of the above application examples.

The medical apparatus according to this application example is suitable for the use as a surgical instrument for excising or incising a living tissue. When the operation unit is held in the hand and thus operated, the movement of the operation unit is detected by the acceleration sensor and is compared with the preset acceleration that is set on the basis of the selected ejection mode, thus controlling ejection of the fluid. Therefore, the operator can perform appropriate incision or excision as the operator intends, whether in the case where a broad range is to be cut superficially or in the case where a narrow range is to be cut to an appropriate depth. The operation can be made easier and safety can be improved.

APPLICATION EXAMPLE 7

This application example of the invention is directed to a fluid ejection method for ejecting a fluid to incise or excise a target. The method includes: supplying the fluid; allowing a predetermined ejection mode to be selected; detecting an acceleration of an operation unit held by a user; and controlling ejection of the supplied fluid, using a preset acceleration that is set on the basis of the ejection mode that is selected, and the operation acceleration that is detected.

According to this application example, the movement (operation acceleration) at the time when the operator operates the operation unit is detected, and the preset acceleration that is set on the basis of the selected ejection mode is compared with the operation acceleration, thus controlling ejection of the fluid. Therefore, the operator can perform appropriate incision or excision as the operator intends, for example, whether in the case where a broad range is to be cut superficially or in the case where a narrow range is to be cut to an appropriate depth.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described with reference to the drawings.

The drawings referred to in the following description are schematic views in which each member is depicted in sizes that make each member recognizable and therefore the longitudinal and lateral scales of each member or part are different from actual scales thereof.

Embodiment 1

Figure 1:
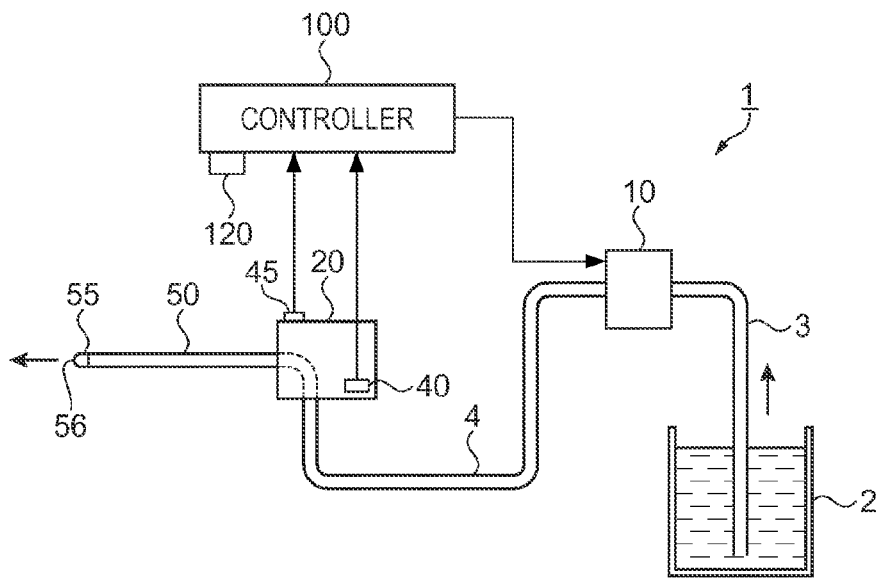
FIG. 1 is a configuration view schematically showing a fluid ejection device according to Embodiment 1.

FIG. 1 is a configuration view schematically showing a fluid ejection device 1 according to Embodiment 1. In FIG. 1, the fluid ejection device 1 includes a fluid supplying unit 10 which sucks in a fluid from a fluid container 2 housing the fluid via a first connection tube 3, a fluid ejection tube 50 which causes the fluid supplied from the fluid supplying unit 10 to be ejected, a second connection tube 4 connecting the fluid ejection tube 50 and the fluid supplying unit 10, and a controller 100 which controls the ejection of the fluid.

Here, the fluid supplying unit 10 is a pump and the form of the pump is not particularly limited. At a forward edge of the fluid ejection tube 50, a nozzle 55 having a fluid ejection opening 56 with a reduced channel diameter is inserted and the supply pressure of the fluid supplying unit 10 is further increased by the nozzle 55. Thus, high-speed ejection from the fluid ejection opening 56 is possible. Therefore, it is desirable that the fluid ejection tube 50 is rigid enough to avoid deformation due to fluid ejection or deformation in operation, and that the second connection tube 4 is flexible enough to enable free operation.

At the connecting part between the fluid ejection tube 50 and the second connection tube 4, an operation unit 20 with a shape and weight which the operator can easily grasp with the hand is provided (FIG. 1 shows a simplified depiction).

On the operation unit 20, an acceleration sensor 40 which detects movements of the operation unit 20, and an ejection switch 45 by which the user inputs a command to eject or not to eject are installed. As the acceleration sensor 40, a sensor is used which can detect accelerations of movements on planes perpendicular to the axial direction of the fluid ejection tube 50 (hereinafter referred to as operation acceleration) and therefore can detect at least two axes. The installing position of the acceleration sensor 40 is not limited to the position shown and may be an arbitrary position in the operation unit 20 or an arbitrary position in the fluid ejection tube 50. As the installing position of the ejection switch 45, the operator can select an arbitrary position that makes operation easier. To give a command to eject, ON is inputted to the ejection switch 45. To give a command not to eject, OFF is inputted. The ejection switch 45 outputs a command signal according to ON or OFF that is inputted.

The controller 100 receives a detection signal from the acceleration sensor 40 and an input signal from the ejection switch 45, and controls driving of the fluid supplying unit 10 based on these signals, thus controlling fluid ejection. The controller 100 is provided with an ejection mode selecting unit 120. The ejection mode selecting unit 120 includes a switch or dial by which the user selects an ejection mode for incision or excision over a broad range (broad range mode) or an ejection mode for incision or excision in a narrow range (narrow range mode). The attaching position of the ejection mode selecting unit 120 may be other than on the controller 100. The ejection mode selecting unit 120 may be arranged at an arbitrary position on the operation unit 20 or may be arranged independently. The configuration of the controller 100 will be described in detail with reference to FIG. 2.

Figure 2:
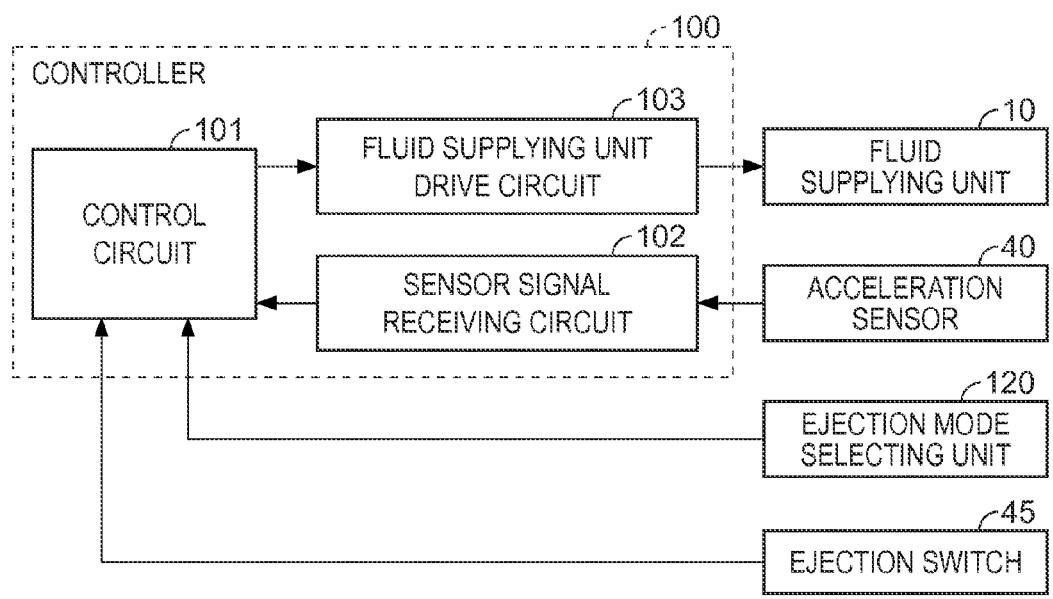
FIG. 2 is an explanatory view of configuration showing the main configuration of a controller.

FIG. 2 is an explanatory view of configuration showing the main configuration of the controller 100. The controller 100 includes a control circuit 101 which performs overall control of the fluid ejection device 1, a fluid supplying unit drive circuit 103 which controls driving of the fluid supplying unit 10 (controls whether to eject the fluid or not), and a sensor signal receiving circuit 102 which receives an operation acceleration detecting signal from the acceleration sensor 40.

The control circuit 101 has a circuit which processes an input signal from the ejection switch 45, a circuit which processes an input signal from the ejection mode selecting unit 120, a storage circuit which stores a preset acceleration that is set in advance based on the ejection mode, and the like (not shown).

The control circuit 101 controls the device in a state where fluid ejection can be performed according to the input of whether to eject or not from the ejection switch 45 and the ejection mode selected by the ejection mode selecting unit 120. The control circuit 101 determines whether the operation acceleration detected by the acceleration sensor 40 is greater than the preset acceleration or not, and controls driving of the fluid supplying unit 10 based on the result of the determination.

Next, a fluid ejection control method according to Embodiment 1 will be described with reference to the drawings.

First, a control method in the case where the broad range mode is selected by the ejection mode selecting unit 120 will be described.

Figure 3:
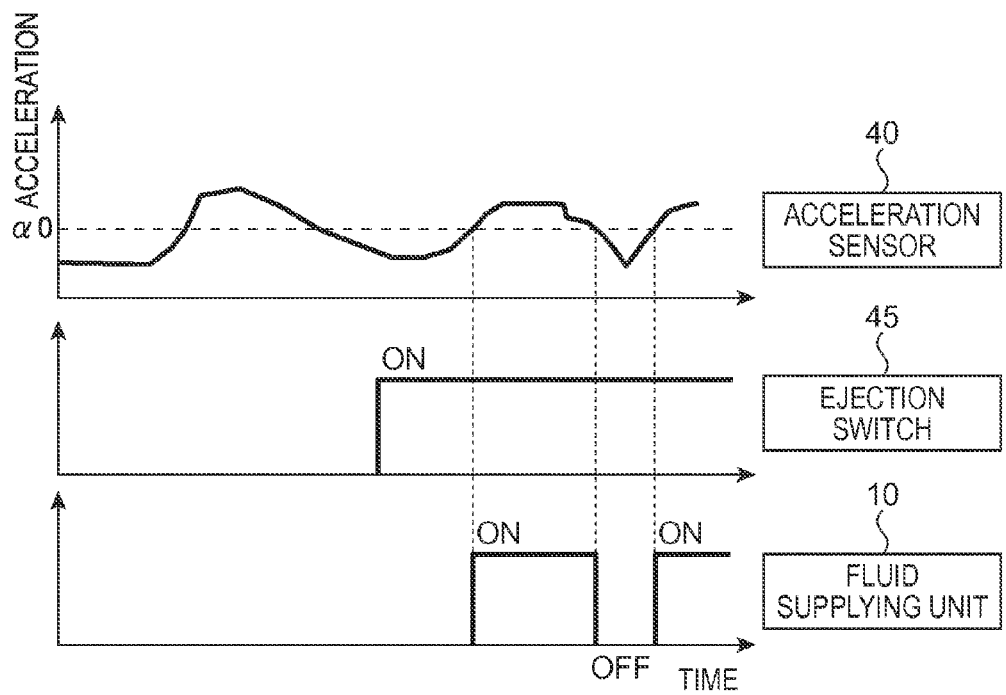
FIG. 3 is an explanatory view showing a specific example of fluid ejection based on the algorithm of Table 1.

Table 1 shows an algorithm for fluid ejection control in the broad range mode. FIG. 3 is an explanatory view showing a specific example of fluid ejection based on the algorithm of Table 1. The control method is described with reference to Table 1 and FIG. 3. The preset acceleration that is set in advance is $\alpha 0$. The operation acceleration detected by the acceleration sensor 40 is $\alpha$.

TABLE 1

| Ejection switch | Acceleration sensor | Fluid supplying unit |
| --- | --- | --- |
| ON | $\alpha 0 < \alpha$ | ON |
| ON | $\alpha 0 > \alpha$ | OFF |
| OFF | $\alpha 0 < \alpha$ | OFF |
| OFF | $\alpha 0 > \alpha$ | OFF |

The acceleration sensor 40 detects the acceleration of the operation unit 20 irrespective of whether ejection is permitted or not (that is, irrespective of whether operation is carried out or not). Here, while the ejection switch 45 is ON, the fluid supplying unit 10 is driven (ON) if $\alpha 0 < \alpha$, and the fluid supplying unit 10 is stopped (OFF) if $\alpha 0 > \alpha$. When the ejection switch 45 is OFF, driving of the fluid supplying unit 10 is stopped in both cases of $\alpha 0 < \alpha$ and $\alpha 0 > \alpha$. That is, the fluid is ejected when the signal from the ejection switch 45 is ON and the operation acceleration $\alpha$ is greater than the preset acceleration $\alpha 0$. The ejection of the fluid is stopped when the signal from the ejection switch 45 is ON and the operation acceleration $\alpha$ is smaller than the preset acceleration $\alpha 0$.

If $\alpha 0 = \alpha$, the fluid supplying unit 10 is preferably set to be stopped (OFF) in order to prioritize safety.

According to the above control method, when a relatively broad range is to be cut superficially, the operation acceleration $\alpha$ and the preset acceleration $\alpha 0$ are compared and determined, and whether to eject the fluid or not is thus controlled. Thus, as the operation unit 20 is moved finely and quickly, the fluid is ejected. As the movement of the hand is slowed down or stopped, the ejection of the fluid is stopped. Therefore, ejection is not carried out continuously at the same spot and unnecessarily deep cutting can be prevented.

Next, a control method in the case where the narrow range mode is selected by the ejection mode selecting unit 120 will be described.

Figure 4:
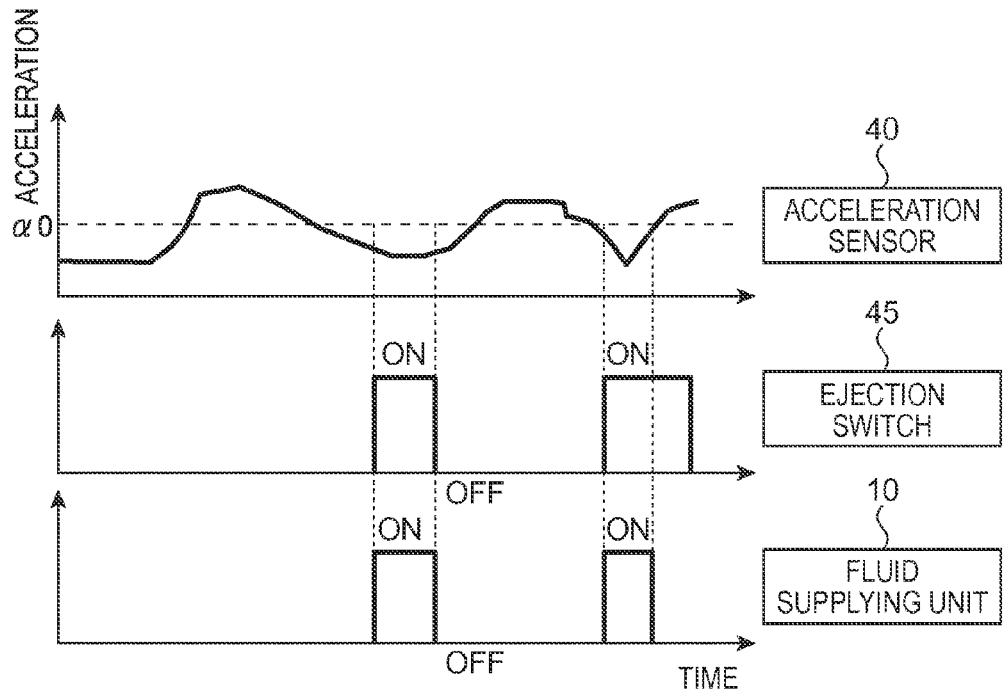
FIG. 4 is an explanatory view showing a specific example of fluid ejection based on the algorithm of Table 2.

Table 2 shows an algorithm for fluid ejection control in the narrow range mode. FIG. 4 is an explanatory view showing a specific example of fluid ejection based on the algorithm of Table 2. The control method is described with reference to Table 2 and FIG. 4. The preset acceleration that is set in advance is $\alpha 0$. The operation acceleration detected by the acceleration sensor 40 is $\alpha$.

TABLE 2

| Ejection switch | Acceleration sensor | Fluid supplying unit |
| --- | --- | --- |
| ON | $\alpha 0 < \alpha$ | OFF |
| ON | $\alpha 0 > \alpha$ | ON |
| OFF | $\alpha 0 < \alpha$ | OFF |
| OFF | $\alpha 0 > \alpha$ | OFF |

The acceleration sensor 40 detects the acceleration of the operation unit 20 irrespective of whether ejection is permitted or not (that is, irrespective of whether operation is carried out or not). Here, while the ejection switch 45 is ON, the fluid supplying unit 10 is stopped (OFF) if $\alpha 0 < \alpha$, and the fluid supplying unit 10 is driven (ON) if $\alpha 0 > \alpha$. When the ejection switch 45 is OFF, driving of the fluid supplying unit 10 is stopped in both cases of $\alpha 0 < \alpha$ and $\alpha 0 > \alpha$. That is, the ejection of the fluid is stopped when the signal from the ejection switch 45 is ON and the operation acceleration $\alpha$ is greater than the preset acceleration $\alpha 0$. The fluid is ejected when the signal from the ejection switch 45 is ON and the operation acceleration $\alpha$ is smaller than the preset acceleration $\alpha 0$.

If $\alpha 0 = \alpha$, the fluid supplying unit 10 is preferably set to be stopped (OFF) in order to prioritize safety.

According to the above control method, when a specific site is to be excised or incised, the narrow range mode is selected as the ejection mode and the ejection switch 45 is turned on. When the movement of the operation unit 20 is small ($\alpha<\alpha 0$), excision can be performed. If the hand accidentally shakes and makes a large movement and the operation acceleration $\alpha$ is determined as greater than the preset acceleration $\alpha 0$, the ejection is stopped. Thus, excision of an unintended site can be prevented.

Embodiment 2

Next, a fluid ejection device 1 and a fluid ejection control method according to Embodiment 2 will be described. In Embodiment 2, a pulse flow is used instead of the continuous flow for fluid ejection in the above Embodiment 1.

Figure 5:
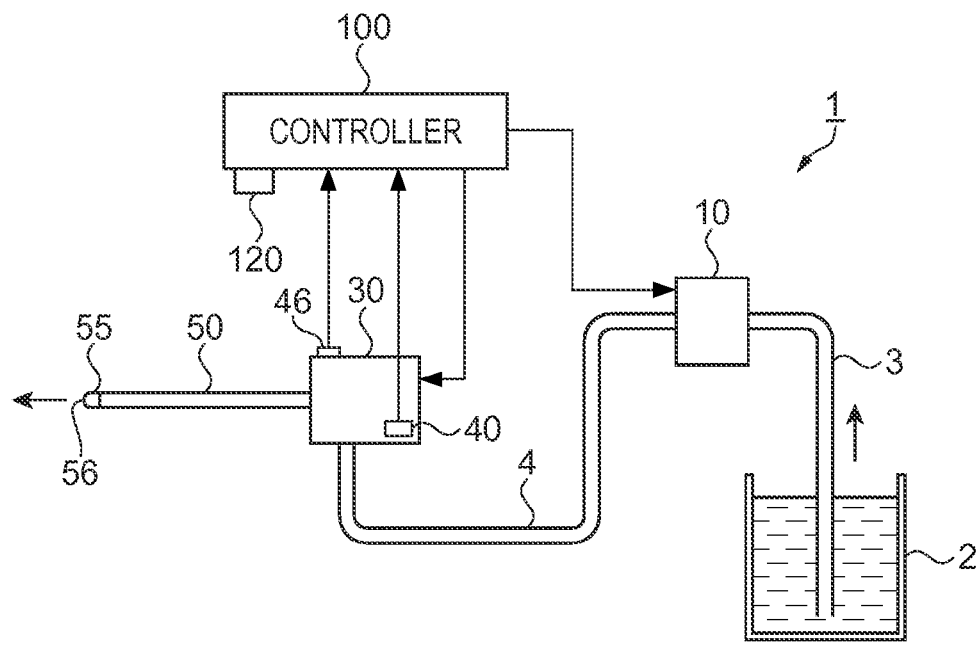
FIG. 5 is a configuration view schematically showing a fluid ejection device according to Embodiment 2.

FIG. 5 is a configuration view schematically showing the fluid ejection device 1 according to Embodiment 2. In FIG. 5, the fluid ejection device 1 includes a fluid supplying unit 10 which sucks in a fluid from a fluid container 2 housing the fluid via a first connection tube 3, a pulsation generator 30 which generates pulsation in the fluid supplied from the fluid supplying unit 10, a fluid ejection tube 50 continuing to the pulsation generator 30, a second connection tube 4 connecting the fluid supplying unit 10 and the pulsation generator 30, and a controller 100 which controls the ejection of the fluid.

Here, the fluid supplying unit 10 is a pump and the form of the pump is not particularly limited. At a forward edge of the fluid ejection tube 50, a nozzle 55 having a fluid ejection opening 56 with a reduced channel diameter is inserted. Using the pulsation flow generated by the pulsation generator 30 as a pulse flow, high-speed ejection from the fluid ejection opening 56 is carried out. Therefore, it is desirable that the fluid ejection tube 50 is rigid enough to avoid deformation due to fluid ejection or deformation in operation, and that the second connection tube 4 is flexible enough to enable free operation. The pulsation generator 30 is an operation unit for the operator to hold in the hand to operate, and may be covered with a casing that can be grasped easily.

On the pulsation generator 30, an acceleration sensor 40 which detects movements of the pulsation generator 30, and an ejection switch for inputting a command to eject or not to eject (referred to as a pulse ejection switch 46 in order to distinguish from Embodiment 1) are installed. As the acceleration sensor 40, a sensor is used which can detect operation accelerations of movements on planes perpendicular to the axial direction of the fluid ejection tube 50 and therefore can detect at least two axes, as in Embodiment 1. The installing position of the acceleration sensor 40 is not limited to the position shown and may be an arbitrary position in the pulsation generator 30 or an arbitrary position in the fluid ejection tube 50. Also, as the installing position of the pulse ejection switch 46, the operator can select an arbitrary position that makes operation easier. The controller 100 is provided with a main switch (not shown) to start up the controller 100.

The controller 100 is a controller which controls ejection of a pulse fluid. The controller 100 receives a detection signal from the acceleration sensor 40 and an input signal from the pulse ejection switch 46, and controls driving of the fluid supplying unit 10 and the pulsation generator 30 based on these signals, thus controlling whether to perform pulse ejection or not. The controller 100 is provided with an ejection mode selecting unit 120. The ejection mode selecting unit 120 includes a switch or dial for selecting an ejection mode for incision or excision over a broad range or an ejection mode for incision or excision in a narrow range. The attaching position of the ejection mode selecting unit 120 may be other than on the controller 100. The ejection mode selecting unit 120 may be arranged at an arbitrary position on the pulsation generator 30 or maybe arranged independently. The detailed configuration of the controller 100 will be described later with reference to FIG. 7.

Next, the configuration of the pulsation generator will be described with reference to the drawings.

Figure 6:
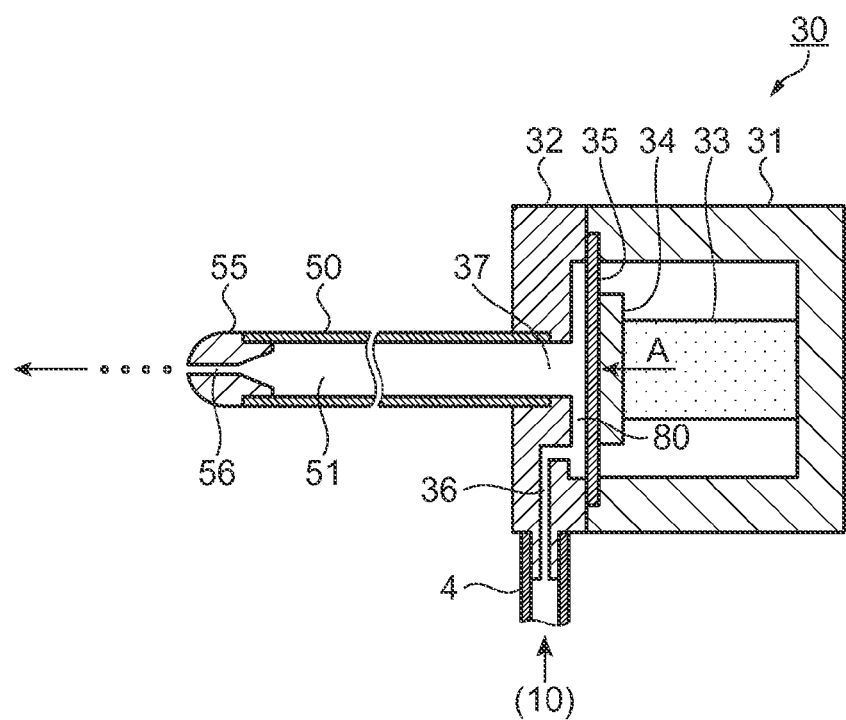
FIG. 6 is a sectional view showing the configuration of a pulsation generator according to Embodiment 2.

FIG. 6 is a sectional view showing the configuration of the pulsation generator 30. In FIG. 6, pulsation generator 30 includes a piezoelectric element 33 as a volume varying unit for a fluid chamber 80, a diaphragm 35, and the fluid ejection tube 50 having an ejection channel 51 continuing to the fluid chamber 80.

The piezoelectric element 33 is arranged within a space of a first case 31. One end of the piezoelectric element 33 is fixed to a bottom section of the first case 31, and the other end is fixed to the diaphragm 35 via a reinforcing plate 34. As the piezoelectric element 33, a piezoelectric element is employed which expands in the direction of arrow A when electric charge is applied and which contracts and restore its initial length when electric charge is removed.

An inlet channel 36 continues to the fluid chamber 80. The inlet channel 36 is connected to the fluid supplying unit 10 via the second connection tube 4.

The fluid ejection tube 50 has the ejection channel 51 continuing to an outlet channel 37 formed in a second case 32. The nozzle 55 having the fluid ejection opening 56 with a reduced channel diameter is inserted at the forward end of the fluid ejection tube 50.

Next, the configuration of the controller 100 will be described.

Figure 7:
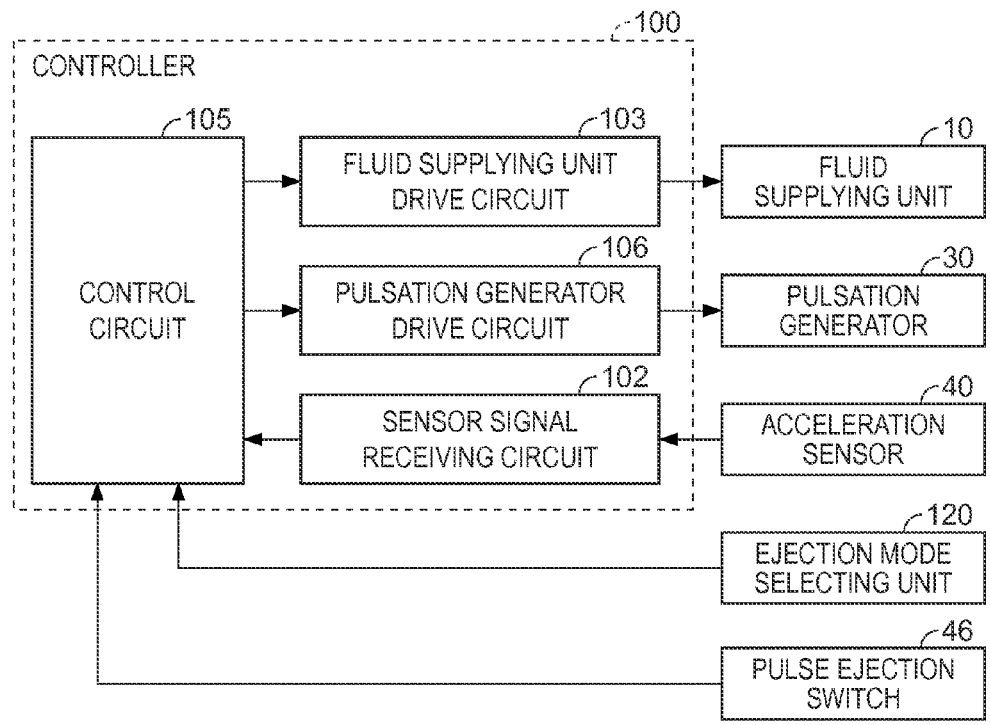
FIG. 7 is an explanatory view of configuration showing the main configuration of a controller according to Embodiment 2.

FIG. 7 is an explanatory view of configuration showing the main configuration of the controller 100 according to Embodiment 2. The components with the same functions as in Embodiment 1 are denoted by the same reference numerals and will not be described further in detail. The controller 100 includes a control circuit 105 which performs overall control of the fluid ejection device 1, a fluid supplying unit drive circuit 103 which controls driving of the fluid supplying unit 10, a sensor signal receiving circuit 102 which receives an operation acceleration detecting signal from the acceleration sensor 40, and a pulsation generator drive circuit 106 which controls driving of the pulsation generator 30.

The control circuit 105 has a circuit which processes an input signal from the pulse ejection switch 46, a circuit which processes an input signal from the ejection mode selecting unit 120, a storage circuit which stores a preset acceleration that is set in advance based on the ejection mode, and the like (not shown).

The control circuit 105 controls the device in a state where pulse flow ejection can be performed according to the input of whether to eject or not from the pulse ejection switch 46 and the ejection mode selected by the ejection mode selecting unit 120. The control circuit 105 determines whether the operation acceleration detected by the acceleration sensor 40 is greater than the preset acceleration or not, and controls driving of the fluid supplying unit 10 and the pulsation generator 30 based on the result of the determination.

Next, the action of pulse flow ejection in this embodiment will be described with reference to FIG. 5 and FIG. 6. A fluid is supplied to the fluid chamber 80 with a predetermined hydraulic pressure by the fluid supplying unit 10. Consequently, when no operation is carried out on the piezoelectric element 33, the fluid flows into the fluid chamber 80 due to the difference between a discharge force of the fluid supplying unit 10 and an overall fluid resistance value on the side of the inlet channel 36, and a continuous flow is ejected from the fluid ejection opening 56.

When a drive waveform is inputted to the piezoelectric element 33, the volume of the fluid chamber 80 is varied by the diaphragm 35 according to the expansion or contraction of the piezoelectric element 33. That is, if a drive signal is inputted to the piezoelectric element 33 and the piezoelectric element 33 expands, the pressure within the fluid chamber 80 rises and reaches several tens of atmospheres. Meanwhile, if the drive signal is stopped, the piezoelectric element 33 contracts and the pressure within the fluid chamber 80 falls. A pulsation flow is generated by this pressure fluctuation in the fluid chamber 80. The pressure fluctuation in this case propagates through the fluid ejection tube 50 and the fluid is ejected at a high speed in a pulsed form from the fluid ejection opening 56 at the forward end. Here, the pulsation flow means the flow of the fluid in which the flow rate or flow speed of the fluid fluctuates cyclically or irregularly. The pulsation flow may include an intermittent flow in which the flow and pause of the fluid is repeated. However, it suffices that the flow rate or flow speed of the fluid fluctuates cyclically or irregularly. Similarly, ejecting the fluid in a pulsed form means the ejection of the fluid in which the flow rate or traveling speed of the ejected fluid fluctuates cyclically or irregularly.

Next, a voltage waveform inputted to the piezoelectric element 33 will be described.

Figure 8:
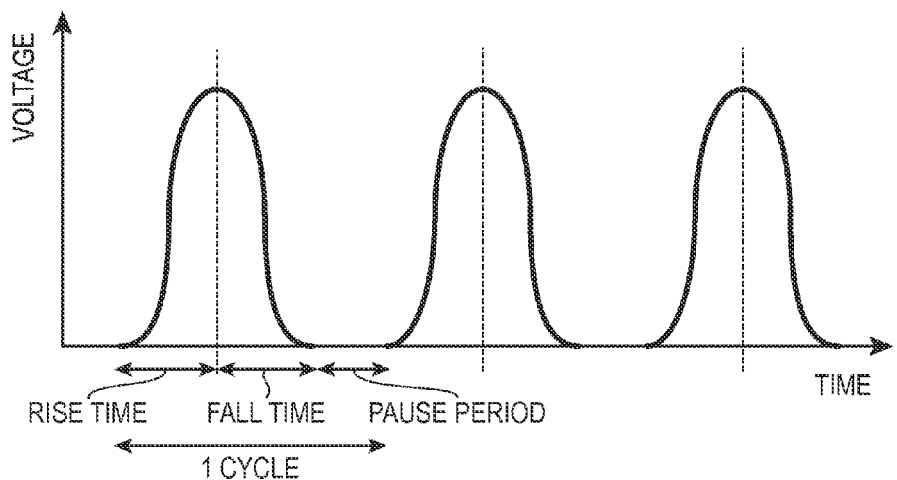
FIG. 8 shows an example of a voltage waveform inputted to a piezoelectric element.

FIG. 8 shows an example of a voltage waveform inputted to the piezoelectric element 33. A drive waveform is a combination of a sin waveform (corresponding to one cycle) with its phase shifted by −90 degrees by an offset in a positive voltage direction, and a pause period. To raise the repetition frequency of this drive waveform, the duration of the pause period can be changed. For example, on the assumption that the piezoelectric element 33 used for the volume varying unit expands when a positive voltage is applied thereto, the rise time of the drive waveform is equivalent to the time period when the volume of the fluid chamber 80 is reduced. The fall time of the drive waveform is equivalent to the time period when the volume of the fluid chamber 80 is increased. During the pause period, the volume of the fluid chamber 80 does not change. By repeating such a voltage waveform, a pulsation flow (pulse flow) is generated.

Next, a fluid ejection control method according to Embodiment 2 will be described with reference to the drawings.

First, a control method in the case where the broad range mode is selected by the ejection mode selecting unit 120 will be described.

Figure 9:
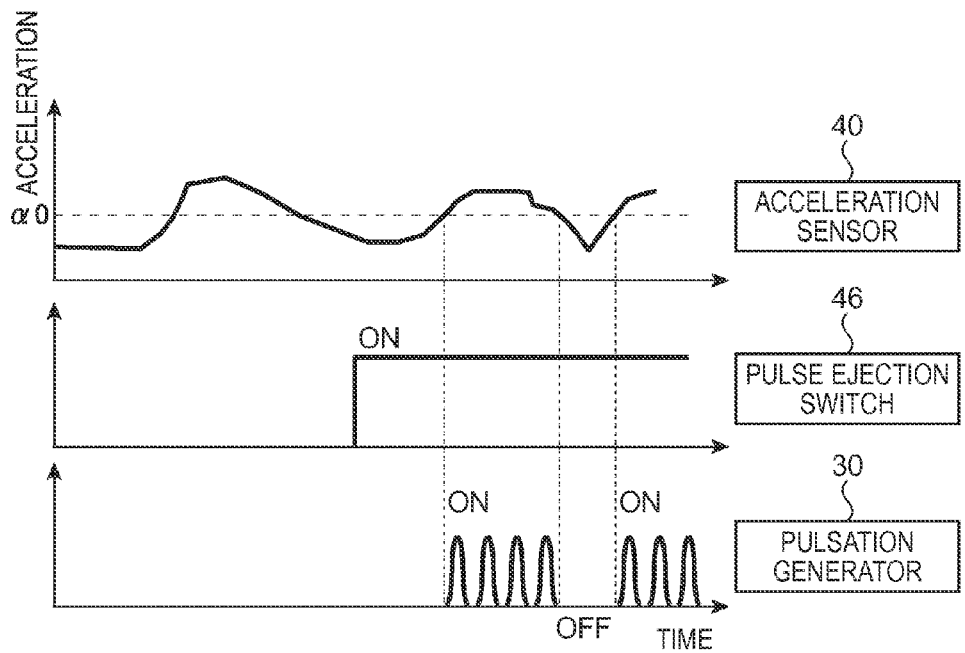
FIG. 9 is an explanatory view showing a specific example of pulse flow ejection based on the algorithm of Table 3.

Table 3 shows an algorithm for pulse flow ejection control in the broad range mode. FIG. 9 is an explanatory view showing a specific example of pulse flow ejection based on the algorithm of Table 3. The control method is described with reference to Table 3 and FIG. 9. The preset acceleration that is set in advance is $\alpha 0$. The operation acceleration detected by the acceleration sensor 40 is $\alpha$.

TABLE 3

| Pulse ejection switch | Acceleration sensor | Fluid supplying unit | Pulsation generator |
|---|---|---|---|
| ON | $\alpha 0 < \alpha$ | ON | ON |
| ON | $\alpha 0 > \alpha$ | ON | OFF |
| OFF | $\alpha 0 < \alpha$ | ON | OFF |
| OFF | $\alpha 0 > \alpha$ | ON | OFF |

First, the controller 100 is started up by the main switch. The fluid supplying unit 10 is driven (the fluid supplying unit ON), and the fluid is supplied to the pulsation generator 30. The acceleration sensor 40 detects the acceleration of the pulsation generator 30 irrespective of whether to eject or not (that is, irrespective of whether operation is carried out or not). Here, while the pulse ejection switch 46 is ON, the pulsation generator 30 is driven (ON) if $\alpha 0 < \alpha$, and the pulsation generator 30 is stopped (OFF) if $\alpha 0 > \alpha$. When the pulse ejection switch 46 is OFF, driving of the pulsation generator 30 is stopped (OFF) in both cases of $\alpha 0 < \alpha$ and $\alpha 0 > \alpha$. That is, the pulse flow is ejected when the signal from the pulse ejection switch 46 is ON and the operation acceleration $\alpha$ is greater than the preset acceleration $\alpha 0$. The ejection of the pulse flow is stopped when the signal from the pulse ejection switch 46 is ON and the operation acceleration $\alpha$ is smaller than the preset acceleration $\alpha 0$.

If $\alpha 0 = \alpha$, the pulsation generator 30 is preferably set to be stopped (OFF) in order to prioritize safety.

According to the above control method, when a relatively broad range is to be cut superficially, the operation acceleration $\alpha$ and the preset acceleration $\alpha 0$ are compared and determined, and ejection is thus controlled. Thus, as the pulsation generator 30 is moved finely and quickly, the fluid is ejected. As the movement of the hand is slowed down or stopped, the ejection of the fluid is stopped. Therefore, ejection is not carried out continuously at the same spot and unnecessarily deep cutting can be prevented.

In the state where the controller 100 is started up by the main switch, even when the pulsation generator 30 is stopped, the fluid supplying unit 10 is driven and continues supplying the fluid to the pulsation generator 30. A continuous flow is ejected from the fluid ejection opening 56. This continuous flow passes through a resistance element within the pulsation generator 30 and therefore has a lower pressure than the pulse flow pressurized by the volume varying unit. Therefore, the ejection of the continuous flow does not cause damage to tissues.

Instead of constantly keeping the fluid supplying unit 10 in the driven state when the main switch is ON, a control method in which driving or non-driving is synchronized between the pulsation generator 30 and the fluid supplying unit 10 may be employed.

Next, a control method in the case where the narrow range mode is selected by the ejection mode selecting unit 120 will be described.

Figure 10:
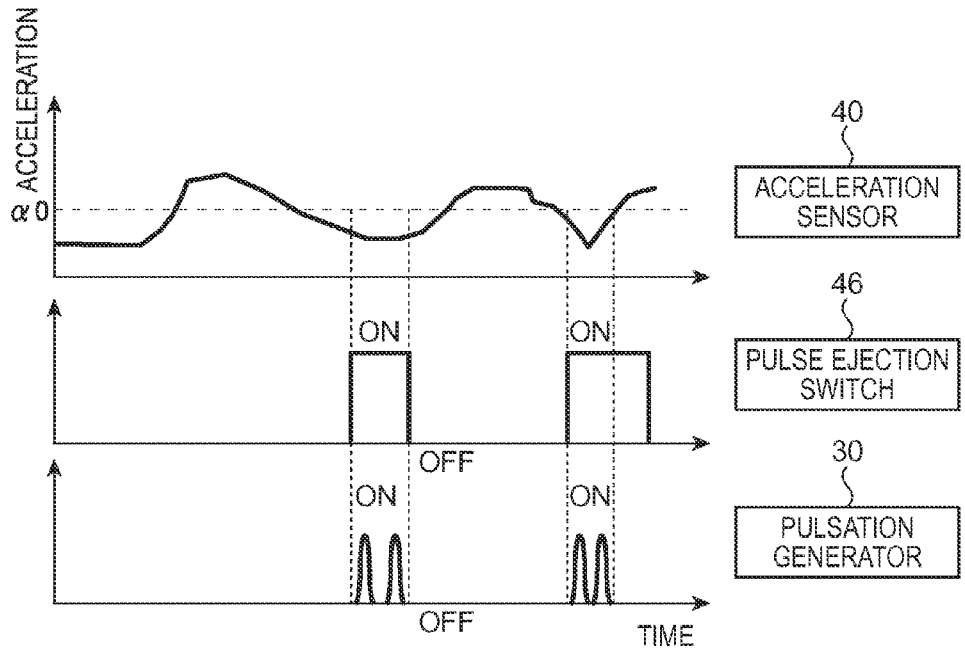
FIG. 10 is an explanatory view showing a specific example of pulse flow ejection based on the algorithm of Table 4.

Table 4 shows an algorithm for fluid ejection control in the narrow range mode. FIG. 10 is an explanatory view showing a specific example of fluid ejection based on the algorithm of Table 4. The control method is described with reference to Table 4 and FIG. 10. The preset acceleration that is set in advance is $\alpha 0$. The operation acceleration detected by the acceleration sensor 40 is $\alpha$.

TABLE 4

| Pulse ejection switch | Acceleration sensor | Fluid supplying unit | Pulsation generator |
|---|---|---|---|
| ON | $\alpha 0 < \alpha$ | ON | OFF |
| ON | $\alpha 0 > \alpha$ | ON | ON |
| OFF | $\alpha 0 < \alpha$ | ON | OFF |
| OFF | $\alpha 0 > \alpha$ | ON | OFF |

The acceleration sensor 40 detects the acceleration of the operation unit irrespective of whether to eject or not (that is, irrespective of whether operation is carried out or not). Here, while the pulse ejection switch 46 is ON, the pulsation generator 30 is stopped (OFF) if $\alpha 0 < \alpha$, and the pulsation generator 30 is driven (ON) if $\alpha 0 > \alpha$. When the pulse ejection switch 46 is OFF, driving of the pulsation generator 30 is stopped (OFF) in both cases of α0<α and α0>α.

If α0=α, the pulsation generator 30 is preferably set to be stopped (OFF) in order to prioritize safety.

According to the above control method, in the case where a specific site is to be excised or incised, excision can be performed when the movement of the pulsation generator 30 is small (operation acceleration α<α0). If the hand accidentally shakes and makes a large movement and the operation acceleration α is determined as greater than the preset acceleration α0, the ejection is stopped. Thus, excision of an unintended site can be prevented.

Embodiment 3

Next, a fluid ejection device according to Embodiment 3 will be described. Embodiment 3 is different from Embodiment 2 in that an information output unit with its output controlled according to the information of the ejection mode and the detection signal (operation acceleration) from the acceleration sensor 40 is provided in Embodiment 3, whereas in Embodiment 2, the ejection of the fluid is controlled according to the signal from the pulse ejection switch 46, the information of the ejection mode and the detection signal from the acceleration sensor 40. Therefore, different features will be mainly described.

Figure 11:
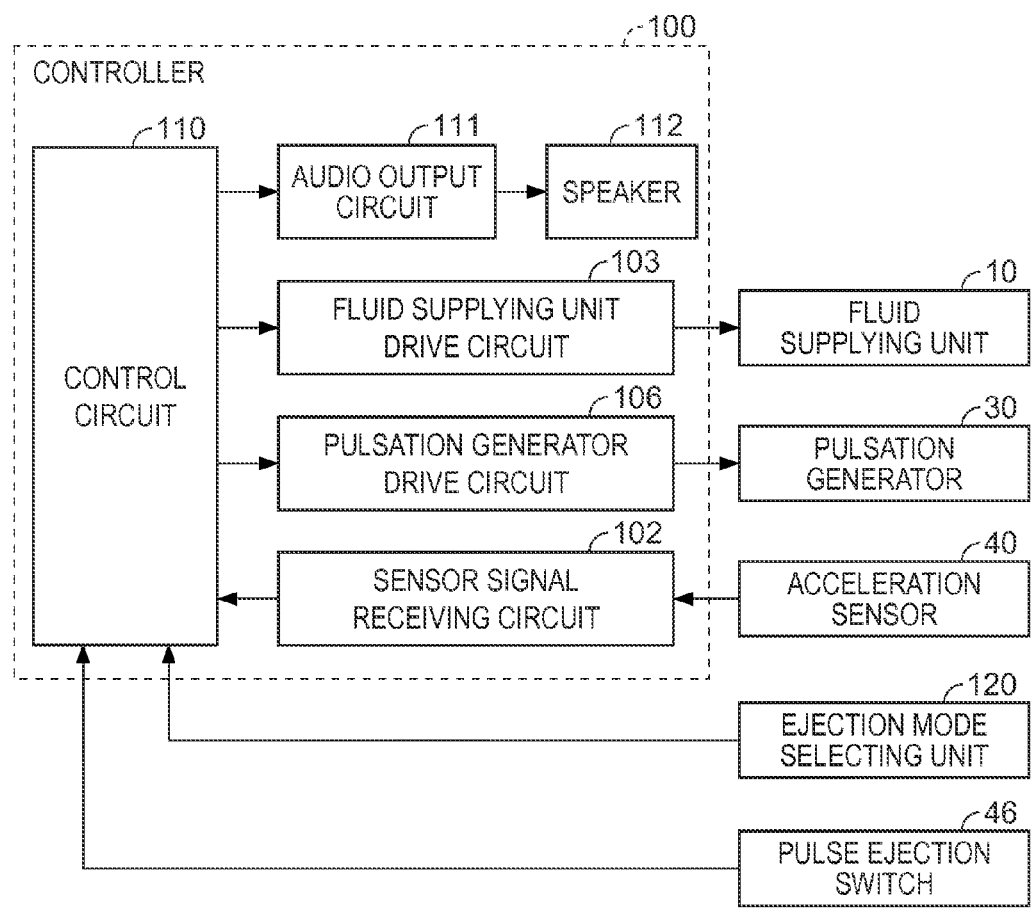
FIG. 11 is an explanatory view of configuration showing the main configuration of a controller according to Embodiment 3.

FIG. 11 is an explanatory view of configuration showing the main configuration of a controller 100 according to Embodiment 3. The sections having the same functions as in Embodiment 2 are denoted by the same reference numerals and will not be described further in detail. The controller 100 includes a control circuit 110 which performs overall control of the fluid ejection device 1, a fluid supplying unit drive circuit 103 which controls driving of a fluid supplying unit 10, a sensor signal receiving circuit 102 which receives an operation acceleration detecting signal from the acceleration sensor 40, a pulsation generator drive circuit 106 which controls driving of a pulsation generator 30, an audio output circuit 111 as an information output unit, and a speaker 112.

As the information output unit, a visually recognizable output unit such as light or screen display may also be used other than a sound. The speaker 112 may be arranged at a different position from the controller 100.

The control circuit 101 has a circuit which processes an input signal from the pulse ejection switch 46, a circuit which processes an input signal from the ejection mode selecting unit 120, a storage circuit which stores a preset acceleration that is set in advance based on the ejection mode and an output content of an audio output, and the like (not shown).

Next, a control method for the information output unit according to Embodiment 3 will be described with reference to the drawings.

First, a control method in the case where the broad range mode is selected by the ejection mode selecting unit 120 will be described.

Figure 12:
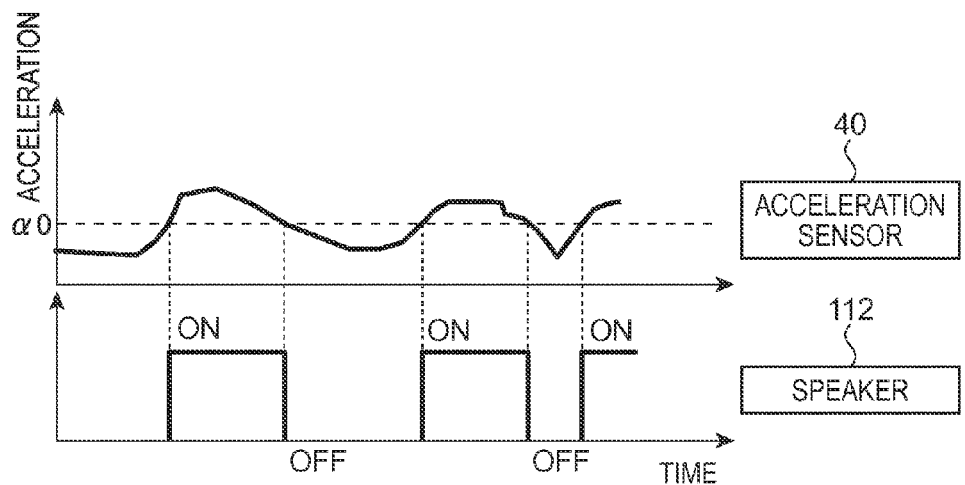
FIG. 12 is an explanatory view showing a specific example of fluid ejection based on the algorithm of Table 5.

Table 5 shows an algorithm for fluid ejection control in the broad range mode. FIG. 12 is an explanatory view showing a specific example of fluid ejection based on the algorithm of Table 5. The control method is described with reference to Table 5 and FIG. 12. The preset acceleration that is set in advance is α0. The operation acceleration detected by the acceleration sensor 40 is α.

TABLE 5

| Pulse ejection switch | Acceleration sensor | Tone |
|---|---|---|
| ON | α0 < α | ON |
| ON | α0 > α | OFF |
| OFF | α0 < α | OFF |
| OFF | α0 > α | OFF |

The acceleration sensor 40 detects the acceleration of the pulsation generator 30 as the operation unit irrespective of whether to eject or not (that is, irrespective of whether operation is carried out or not). Here, while the pulse ejection switch 46 is ON, the pulsation generator 30 is driven (ON) if α0<α, and the pulsation generator 30 is stopped (OFF) if α0>α. When the pulse ejection switch 46 is OFF, driving of the pulsation generator 30 is stopped (OFF) in both cases of α0<α and α0>α. When the pulse ejection switch 46 is ON and α0<α, a sound or tone is outputted from the speaker 112. No tone is outputted if α0>α. That is, if the pulse ejection switch 46 is turned ON when a sound is outputted, fine movement of the pulsation generator 30 leads to ejection of a pulse flow. When no sound is outputted, fluid ejection is stopped even if the pulse ejection switch 46 is turned ON.

Thus, when operation is carried out within the range of α0<α, the user can be notified of whether the current state is suitable for ejection or not, via sound, light, screen display or the like. The user can control the ejection switch according to the output from the information output unit. Therefore, the operator can perform operation under intended ejection conditions.

Next, a control method in the case where the narrow range mode is selected by the ejection mode selecting unit 120 will be described.

Figure 13:
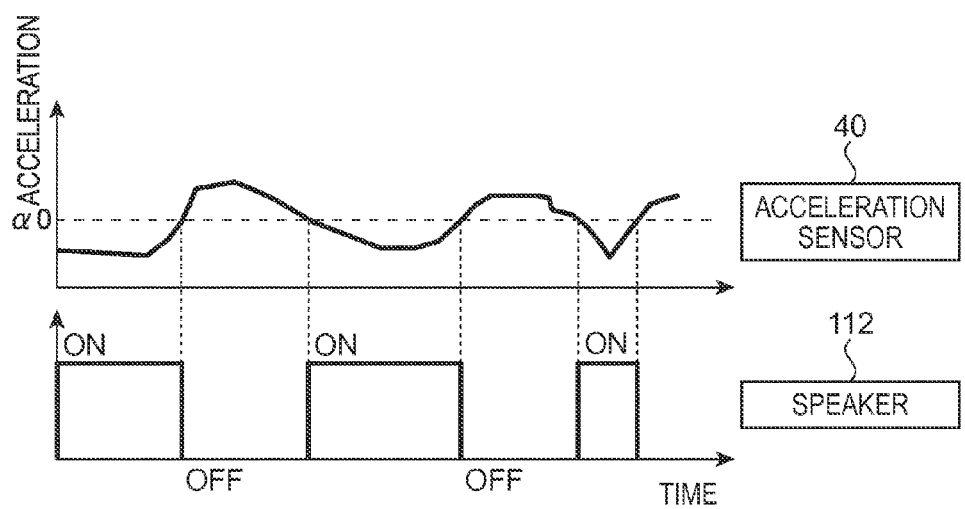
FIG. 13 is an explanatory view showing a specific example of fluid ejection based on the algorithm of Table 6.

Table 6 shows an algorithm for fluid ejection control in the narrow range mode. FIG. 13 is an explanatory view showing a specific example of fluid ejection based on the algorithm of Table 6. The control method is described with reference to Table 6 and FIG. 13. The preset acceleration that is set in advance is α0. The operation acceleration detected by the acceleration sensor 40 is α.

TABLE 6

| Pulse ejection switch | Acceleration sensor | Tone |
|---|---|---|
| ON | α0 < α | OFF |
| ON | α0 > α | ON |
| OFF | α0 < α | OFF |
| OFF | α0 > α | OFF |

The acceleration sensor 40 detects the acceleration of the pulsation generator 30 as the operation unit irrespective of whether to eject or not (that is, irrespective of whether operation is carried out or not). Here, while the pulse ejection switch 46 is ON, the pulsation generator 30 is stopped (OFF) if α0<α, and the pulsation generator 30 is driven (ON) if α0>α. When the pulse ejection switch 46 is OFF, driving of the pulsation generator 30 is stopped (OFF) in both cases of α0<α and α0>α. When the pulse ejection switch 46 is ON and α0>α, a sound or tone can be outputted from the speaker 112.

That is, when operation is carried out within the range of α0>α, the user can be notified of whether the current state is suitable for ejection or not, via sound, light, screen display or the like. In the case where a specific site is to be excised, if the pulse ejection switch 46 is turned ON when a tone is outputted, a pulse flow can be ejected to the site to be excised, without accidental shaking of the hand. Thus, the user can control the ejection switch according to the output from the information output unit. Therefore, the operator can perform operation under intended ejection conditions.

The above ON and OFF functions of the speaker 112 are simply one example. Alternatively, by switching the ON and OFF functions of the speaker 112 and using a warning sound indicating the state where the pulse ejection switch 46 must not be turned ON, or by using different tones for ON and OFF of the speaker 112, the operator maybe enabled to distinguish and recognize whether excision is possible or not.

Medical Apparatus

Next, a medical apparatus using the fluid ejection device 1 and the fluid ejection control method according to the above embodiments will be described. The medical apparatus may include the configuration described in Embodiment 1 (see FIG. 1 and FIG. 2), Embodiment 2 (see FIG. 5, FIG. 6 and FIG. 7) or Embodiment 3 (see FIG. 11). The medical apparatus in this example is a surgical instrument which enables selective excision, incision or fragmentation of living tissues. Therefore, the fluid used here includes a liquid such as a physiological saline solution.

As the fluid to be ejected, both a continuous flow and a pulse flow can be selected. However, the medical apparatus has excellent characteristics as a surgical instrument such as the capability to selectively excise, incise or fragment living tissues and the ability to conserve tubular tissues such as blood vessels, particularly when ejecting the fluid in a pulse form at a high speed.

The movement (operation acceleration $\alpha$) at the time when the operator operates the operation unit (operation unit 20 or pulsation generator 30) is detected by the acceleration sensor 40 and is compared with the preset acceleration $\alpha 0$ that is set on the basis of the selected ejection mode, thus controlling whether to eject the fluid or not. Therefore, a medical apparatus as a surgical instrument which enables the operator to perform appropriate incision or excision as the operator intends whether in the case where a broad range is to be cut superficially or in the case where a narrow range is to be cut to an appropriate depth, and which has good operability and high safety, can be realized.

Modifications

The above embodiments may have the following modifications. In the description of the modifications, the same components as in the embodiments are denoted by the same reference numerals and will not be described further in detail. In the embodiments, the fluid ejection device 1 includes the ejection switch 45. However, the ejection switch 45 maybe omitted. For example, if the operation acceleration $\alpha$ of the operation unit (operation unit 20 or pulsation generator 30) detected by the acceleration sensor 40 is greater than the preset acceleration $\alpha 0$ that is set on the basis of the selected ejection mode, that is, if $\alpha 0 < \alpha$, the fluid supplying unit 10 may be driven (ON), and the fluid supplying unit 10 maybe stopped (OFF) if $\alpha 0 \geq \alpha$. Alternatively, the fluid supplying unit 10 may be driven (ON) if $\alpha 0 \geq \alpha$, and the fluid supplying unit 10 may be stopped (OFF) if $\alpha 0 < \alpha$.

In the embodiments, the preset acceleration that is set on the basis of the selected ejection mode is described as uniformly $\alpha 0$. However, the preset acceleration may be variable based on the selected ejection mode. For example, a preset acceleration $\alpha 1$ for the broad range mode and a preset acceleration $\alpha 2$ for the narrow range mode maybe provided. In this case, these preset acceleration may be $\alpha 1 > \alpha 2$ or $\alpha 1 < \alpha 2$.

This application claims priority to Japanese Patent Application No. 2011-003724, filed on Jan. 12, 2011, the entirety of which is hereby incorporated by reference.

What is claimed is:

1. A fluid ejection device for ejecting a fluid to incise or excise a target, the device comprising:
   a fluid supplying unit which supplies the fluid;
   an operation unit to which the fluid supplied from the fluid supplying unit continues;
   a fluid ejection tube which ejects the fluid continuing to the operation unit;
   an ejection mode selecting unit which allows a predetermined ejection mode to be selected;
   an acceleration sensor which detects an operation acceleration of the operation unit; and
   a controller which controls ejection of the fluid, using a preset acceleration that is set on the basis of the ejection mode that is selected, and the operation acceleration detected by the acceleration sensor.

2. A medical apparatus comprising the fluid ejection device according to claim 1.

3. The fluid ejection device according to claim 1, wherein the predetermined ejection mode includes a broad range mode for incising or excising abroad range of the target, and
   in the case where the broad range mode is selected, the controller ejects the fluid when the operation acceleration is greater than the preset acceleration, and stops ejecting the fluid when the operation acceleration is equal to or smaller than the preset acceleration.

4. A medical apparatus comprising the fluid ejection device according to claim 3.

5. The fluid ejection device according to claim 1, wherein the predetermined ejection mode includes a narrow range mode for incising or excising a narrow range of the target, and
   in the case where the narrow range mode is selected, the controller ejects the fluid when the operation acceleration is smaller than the preset acceleration, and stops ejecting the fluid when the operation acceleration is equal to or greater than the preset acceleration.

6. A medical apparatus comprising the fluid ejection device according to claim 5.

7. The fluid ejection device according to claim 1, further comprising an information output unit which outputs information about whether to eject the fluid or not, using the ejection mode that is selected, the preset acceleration and the operation acceleration.

8. A medical apparatus comprising the fluid ejection device according to claim 7.

9. The fluid ejection device according to claim 1, wherein the operation unit is a pulsation generator which generates a pulse fluid, and
   the controller is a controller which controls ejection of the pulse fluid.

10. A medical apparatus comprising the fluid ejection device according to claim 9.

11. A fluid ejection method for ejecting a fluid to incise or excise a target, the method comprising:
    supplying the fluid;
    allowing a predetermined ejection mode to be selected;
    detecting an acceleration of an operation unit held by a user; and
    controlling ejection of the supplied fluid, using a preset acceleration that is set on the basis of the ejection mode that is selected, and the operation acceleration that is detected.

12. The fluid ejection method according to claim 11, wherein the predetermined ejection mode includes a broad range mode for incising or excising a broad range of the target, and in the controlling, in the case where the broad range mode is selected, the fluid is ejected when the operation acceleration is greater than the preset acceleration, and ejection of the fluid is stopped when the operation acceleration is equal to or smaller than the preset acceleration.

13. The fluid ejection method according to claim 11, wherein the predetermined ejection mode includes a narrow range mode for incising or excising a narrow range of the target, and in the controlling, in the case where the narrow range mode is selected, the fluid is ejected when the operation acceleration is smaller than the preset acceleration, and ejection of the fluid is stopped when the operation acceleration is equal to or greater than the preset acceleration.

* * * * *